US010702224B1

United States Patent
Vanhooser

(10) Patent No.: US 10,702,224 B1
(45) Date of Patent: Jul. 7, 2020

(54) POSITIONING GUIDANCE SYSTEM FOR X-RAY EXAMS

(71) Applicant: Jonathan Ross Vanhooser, Edmond, OK (US)

(72) Inventor: Jonathan Ross Vanhooser, Edmond, OK (US)

(*) Notice: Subject to any disclaimer, the term of this patent is extended or adjusted under 35 U.S.C. 154(b) by 0 days.

(21) Appl. No.: 16/791,389

(22) Filed: Feb. 14, 2020

Related U.S. Application Data

(60) Provisional application No. 62/925,394, filed on Oct. 24, 2019.

(51) Int. Cl.
| | | |
|---|---|---|
| *A61B 6/00* | (2006.01) |
| *A61B 6/04* | (2006.01) |
| *H04N 5/32* | (2006.01) |
| *G06F 3/0482* | (2013.01) |
| *A61B 5/00* | (2006.01) |

(52) U.S. Cl.
CPC .......... *A61B 6/0492* (2013.01); *A61B 6/4417* (2013.01); *A61B 6/463* (2013.01); *A61B 6/465* (2013.01); *A61B 6/469* (2013.01); *A61B 6/547* (2013.01); *G06F 3/0482* (2013.01); *H04N 5/32* (2013.01); *A61B 5/0077* (2013.01); *A61B 6/542* (2013.01)

(58) Field of Classification Search
None
See application file for complete search history.

(56) References Cited

U.S. PATENT DOCUMENTS

| | | | | |
|---|---|---|---|---|
| 2017/0007196 A1* | 1/2017 | Don | ..................... | A61B 6/5264 |
| 2017/0215823 A1* | 8/2017 | Ivanov | ................... | A61B 6/542 |
| 2018/0116613 A1* | 5/2018 | Von Berg | ................ | A61B 8/40 |
| 2018/0197344 A1* | 7/2018 | Takano | ................... | G06T 5/001 |
| 2019/0110768 A1* | 4/2019 | Lee | ...................... | A61B 6/4417 |
| 2019/0380807 A1* | 12/2019 | Addison | ............... | A61B 90/37 |

* cited by examiner

*Primary Examiner* — Hoon K Song
(74) *Attorney, Agent, or Firm* — Tomlinson McKinstry, P.C.

(57) ABSTRACT

A system for assisting an x-ray operator with properly positioning a patient's body part to be x-rayed. The system uses a range sensor supported on an x-ray emitter to collect data about the patient's body part to be x-rayed. The collected data is transmitted to a processor and used to create a mapped envelope of the patient's body part. The processor compares the mapped envelope to a selected reference envelope. If the processor determines that the mapped envelope is not fully contained within the reference envelope, the processor will provide the x-ray operator with a negative notification, indicating that the patient's body part needs to be adjusted. If the processor determines that the mapped envelope is fully contained within the reference envelope, the processor will provide the x-ray operator with a positive notification, indicating the patient's body part is ready to be x-rayed.

20 Claims, 9 Drawing Sheets

POSITIONING GUIDANCE SYSTEM FOR X-RAY EXAMS

SUMMARY

The present invention is directed to a system comprising an x-ray emitter having a field of view and a three-dimensional range sensor having a field of view that at least partially overlaps the field of view of the x-ray emitter. The system further comprises a processor having a memory within which a plurality of reference envelopes are stored. The processor is in communication with the range sensor and configured to use data from the range sensor to generate a virtual map that includes a body part within the field of view of the range sensor. The processor is also configured to generate within the virtual map an envelope that closely surrounds the body part and is configured to compare the mapped envelop to a selected reference envelope.

DETAILED DESCRIPTION

Image quality, proper positioning, and patient safety are important factors when capturing x-ray images. The better the final image submitted, the easier it is for a radiologist to properly diagnose the patient from the image. However, obtaining quality and properly positioned images is just as important as limiting a patient's exposure to radiation—the less x-ray images attempted, the better. Thus, it is important for a technician to capture a high quality, properly positioned x-ray image on the first attempt.

In many cases, the x-ray is taken by an inexperienced radiologic technologist, or more likely a poorly qualified office staff member who is not a radiologic technologist at all. In such case, the patient may not be properly positioned, leading to poor quality images being delivered to the radiologist. Alternatively, the patient may be subjected to repeated x-rays in order to obtain a diagnostic readable image. The present disclosure is directed to a system and method for assisting an x-ray operator with properly positioning a patient's body part to be x-rayed.

Figure 1:
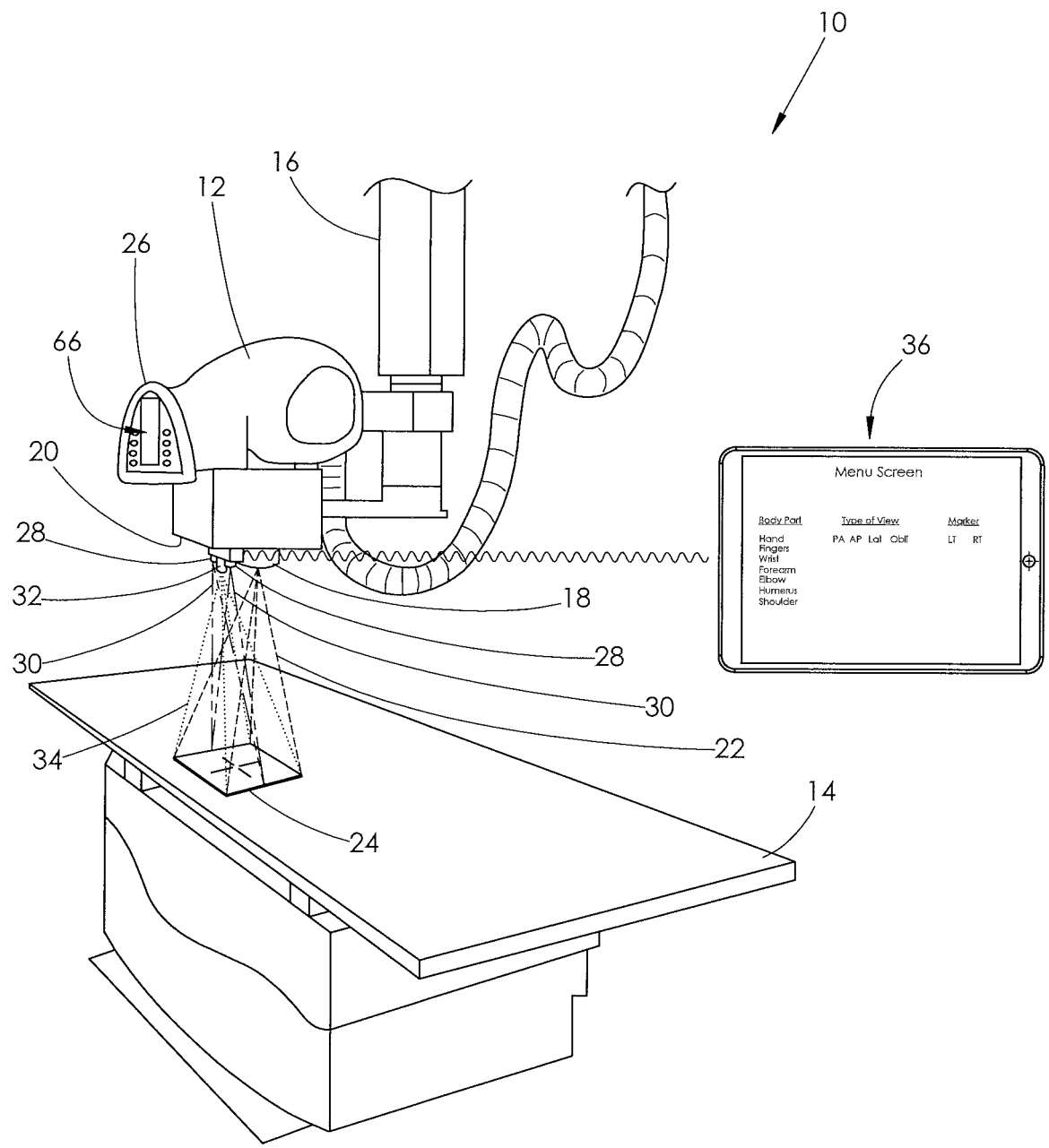
FIG. 1 is an illustration of one embodiment of an x-ray positioning system.

With reference to FIG. 1, one embodiment of an x-ray positioning system 10 is shown. The system 10 comprises an x-ray emitter 12 suspended over a table 14 via an extension arm 16. The x-ray emitter 12 is configured to emit x-ray beams through a window 18 on a bottom surface 20 of the emitter 12. The beams are projected through the window 18 and onto an object positioned within the window's field of view 22. An x-ray cassette 24 is shown positioned within the window's field of view 22 in FIG. 1. A handle 26 is supported on the front of the x-ray emitter 12 and provides a grip for an x-ray operator to move the x-ray emitter 12 relative to the table 14, as needed.

Figure 2:
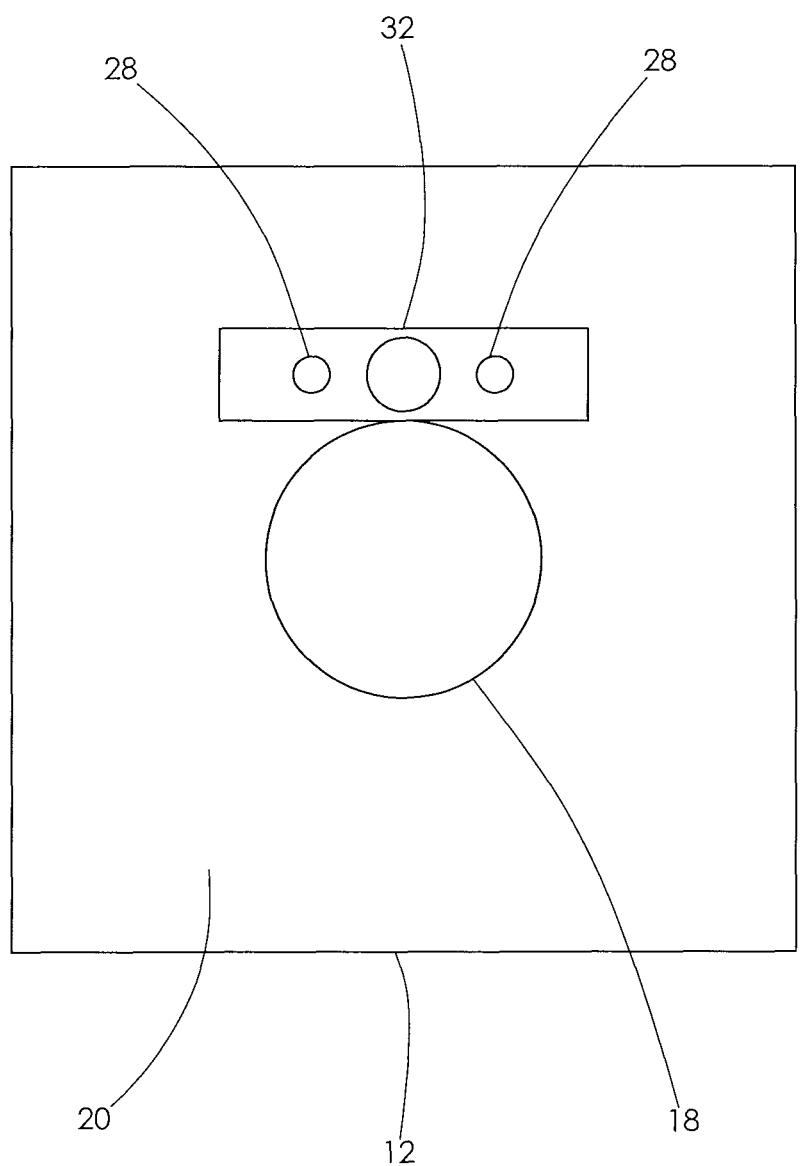
FIG. 2 is a bottom plan view of the x-ray emitter shown in FIG. 1.

With reference to FIGS. 1 and 2, the system 10 further comprises at least one three-dimensional range sensor 28. Two range sensors 28 are shown in FIGS. 1 and 2. However, the system 10 may comprise more than two sensors or only one sensor. The range sensor 28 is preferably a time-of-flight sensor or a sensor that uses infrared light. However, other types of three-dimensional range sensors or may be used. For example a LIDAR, structured light or a stereoscopic sensor may be used.

The range sensor 28 is supported on the bottom surface 20 of the x-ray emitter 12 adjacent the window 18 and has a field of view 30 that at least partially overlaps the window's field of view 22, as shown in FIG. 1. The range sensor 28 is configured to scan objects within its field of view 30 and measure the distance between features of the objects and the sensor 28. In alternative embodiments, the range sensor may be supported on a side of the x-ray emitter, so as long as the range sensor's field of view overlaps the window's field of view.

Continuing with FIGS. 1 and 2, while not required, the system 10 may further comprise an optical camera 32, such as a video camera, positioned adjacent the range sensor 28. As shown in FIG. 1, the camera 32 has a field of view 34 that at least partially overlaps the field of view 22 of the x-ray emitter's window 18 and the field of view 30 of the range sensor 28. If more than one range sensor 28 is used, the sensors 28 may be positioned on opposite sides of the camera 32, as shown for example in FIGS. 1 and 2. The range sensor 28 may also be included as a feature of the camera 32. For example, a time-of-flight camera, LIDAR camera, structured light camera or stereoscopic camera may be used.

Figure 3:
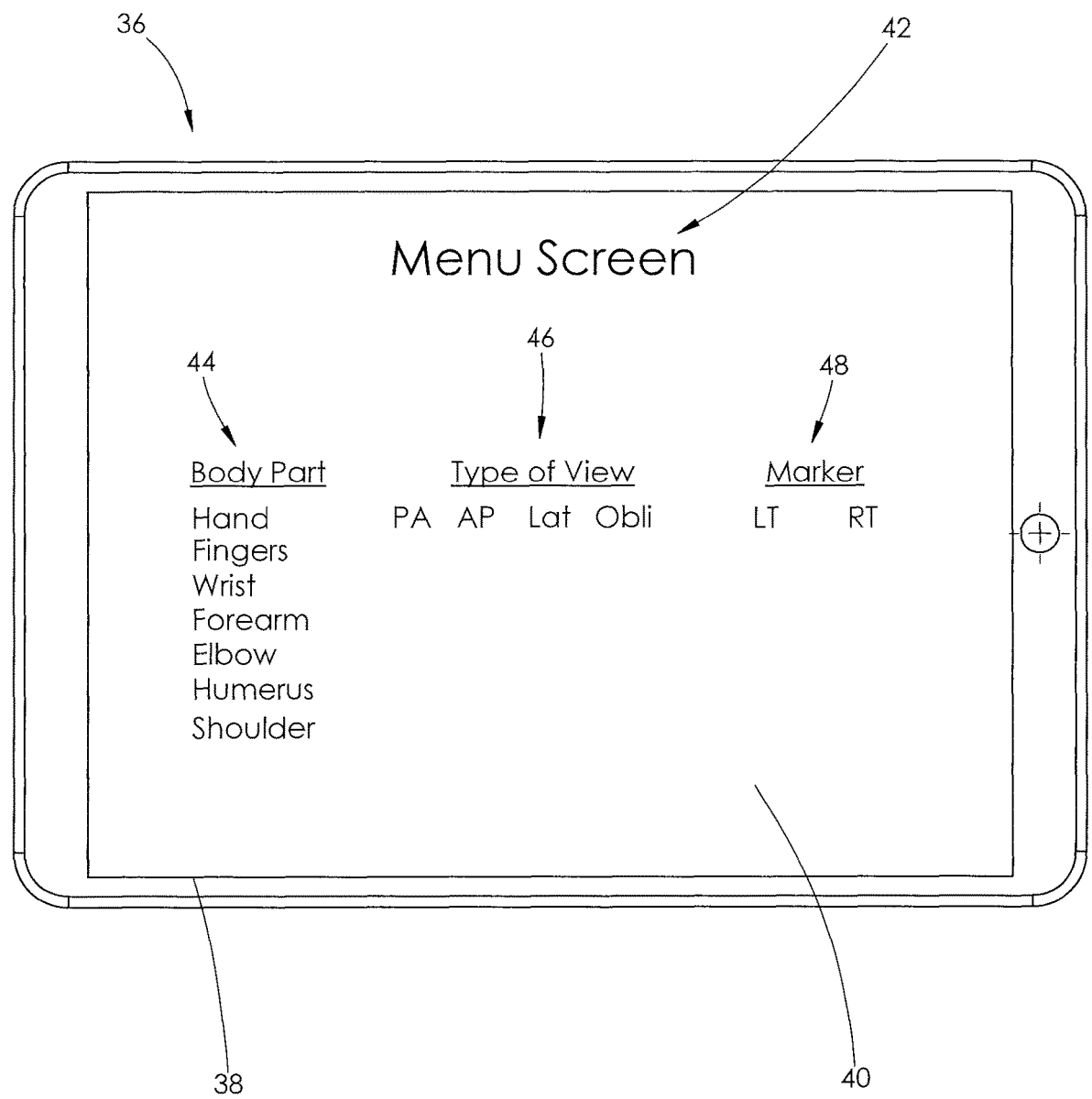
FIG. 3 is an enlarged view of the computer shown in FIG. 1.

Continuing with FIG. 1, the system 10 further comprises a computer 36 having a processor and memory. The computer 36 may be positioned remote from the x-ray emitter 12 and be a desktop, tablet or smartphone. The computer 36 includes a display monitor 38 and an interface 40, as shown in FIG. 3. The computer 36 shown in FIG. 1 is a tablet having a touch screen display. The computer's processor is in communication with the range sensor 28, and if used, the camera 32. Such communication may take place over wires or via a wireless connection. Images captured by the camera 32 may be displayed on the computer's monitor 38.

The system 10 further comprises a plurality of reference envelopes that are stored in the computer's memory. A reference envelope is a three-dimensional virtual envelope that closely surrounds a specifically positioned exemplary body part. The specific position of the body part corresponds with the ideal position of the body part for capturing a desired x-ray view. The computer's memory may have numerous reference envelopes for a single body part—each reference envelope corresponding to a different view. For example, the computer's memory may contain a reference envelope for a posterioranterior (PA), lateral, and oblique view of a left hand. The reference envelopes function as virtual guides for an x-ray operator when positioning a body part in preparation to take an x-ray image.

Figure 4:
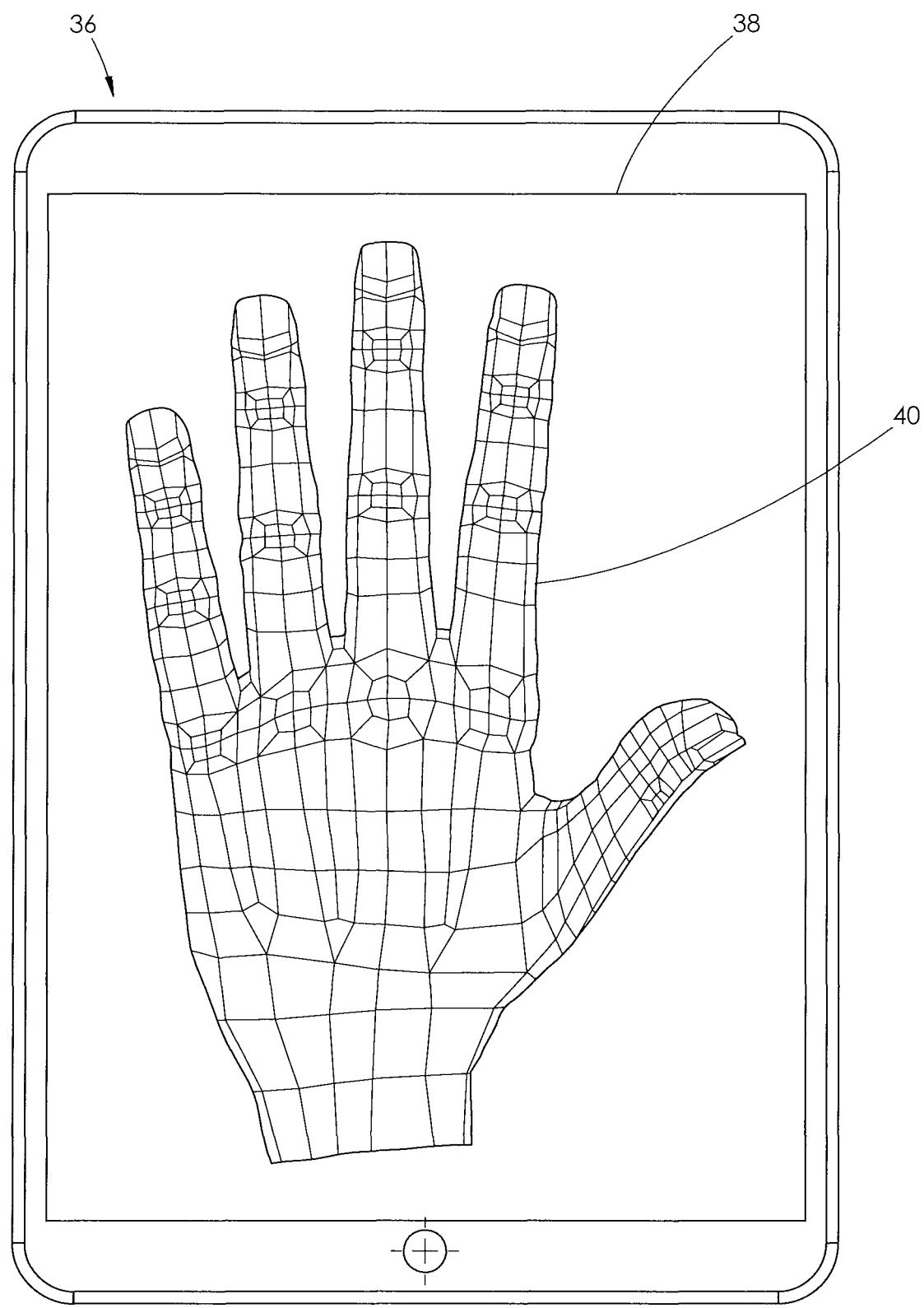
FIG. 4 is the computer shown in FIG. 2. A graphic representation of a reference envelope is displayed on the computer's monitor.

The actual reference envelopes may exist only in coded form and not be visible to an x-ray operator. Alternatively, the reference envelopes may be configured so that a virtual image of a selected reference envelope is displayed on the computer's monitor 38. For example, a virtual image of a reference envelope 40 is shown in FIG. 4. The reference envelope 40 corresponds with a PA view of a left hand.

A desired reference envelope may be selected using a menu 42 displayed on the computer's monitor 38, as shown in FIG. 3. The menu 42 has a selection of body parts 44, a selection of views 46, and a marker selection 48 (right or left side of body). An x-ray operator may select a reference envelope by selecting a body part 44, a desired view 46, and marker 48 from the menu 42. The menu 42 may include more body parts 44 and views 46 than are listed in FIG. 3. Other selections may also be included in the menu 42, as desired.

The plurality of reference envelopes may be created using an x-ray machine and range sensor, like those shown in FIG. 1. A real or phantom body part may be positioned within a field of view of an x-ray emitter and range sensor. The positioning of the body party corresponds with the ideal position for the body part when capturing an image of a specific view. For example, the body part may be positioned by an experienced radiologic technologist.

Once properly positioned, the range sensor may take measurements of all objects within its field of view. The data collected by the range sensor is sent to a computer processor, where it is used to create a virtual three-dimensional map of the objects captured by the range sensor. Using this map, the processor creates a mapped envelope that closely surrounds the body part depicted in the virtual map, thereby creating a reference envelope.

The reference envelopes may also be created by installing a range sensor on a regularly used x-ray emitter. Data may be collected by the range sensor for each x-ray image captured by the emitter. An experienced radiologist may review the images and select a quality, properly positioned image. Data collected by the range sensor related to the selected image may be transmitted to a computer and used to generate a reference envelope.

Figure 5:
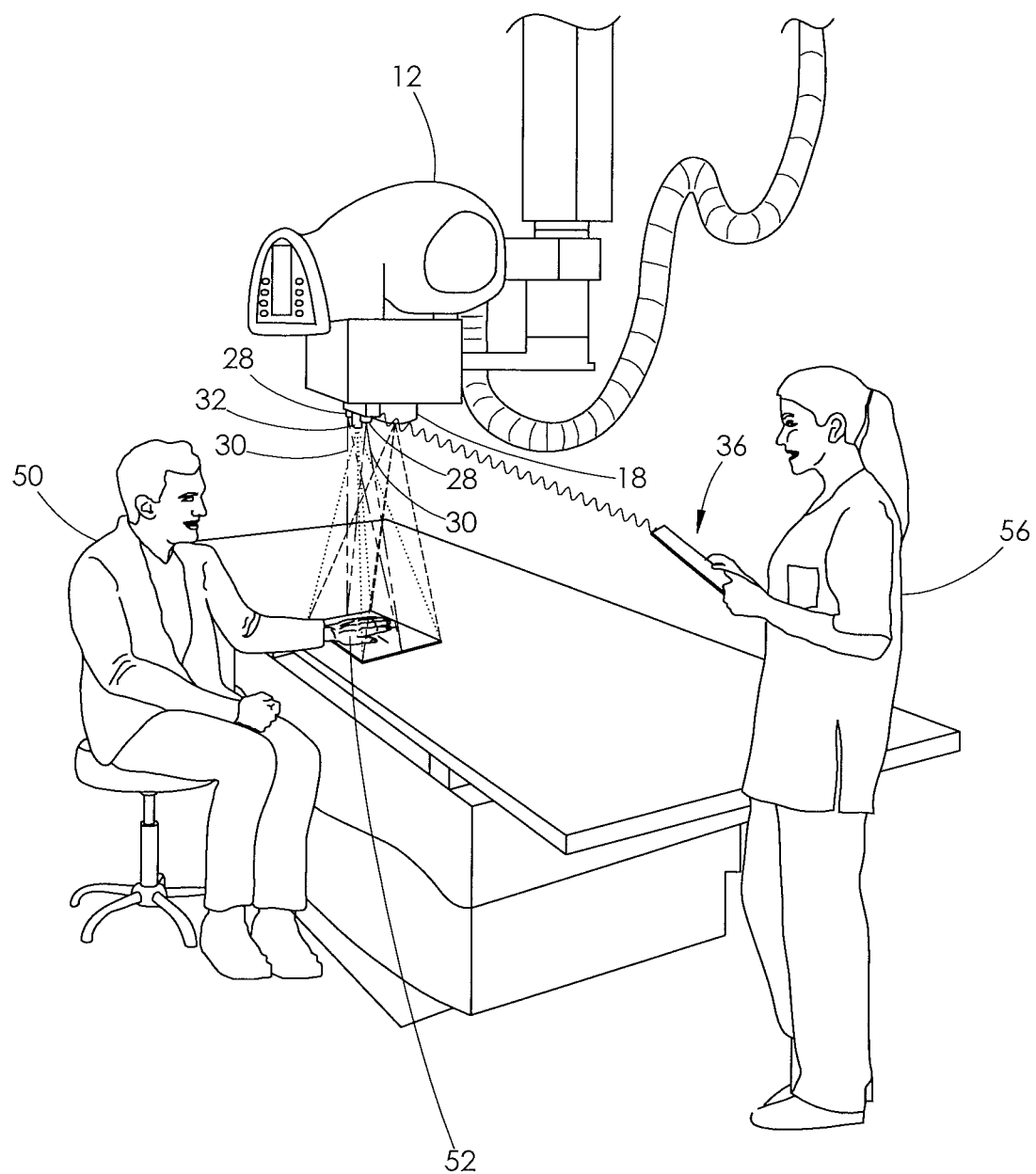
FIG. 5 is the system shown in FIG. 1, with a patient having his hand below the x-ray emitter and an x-ray operator holding the computer.
Figure 6:
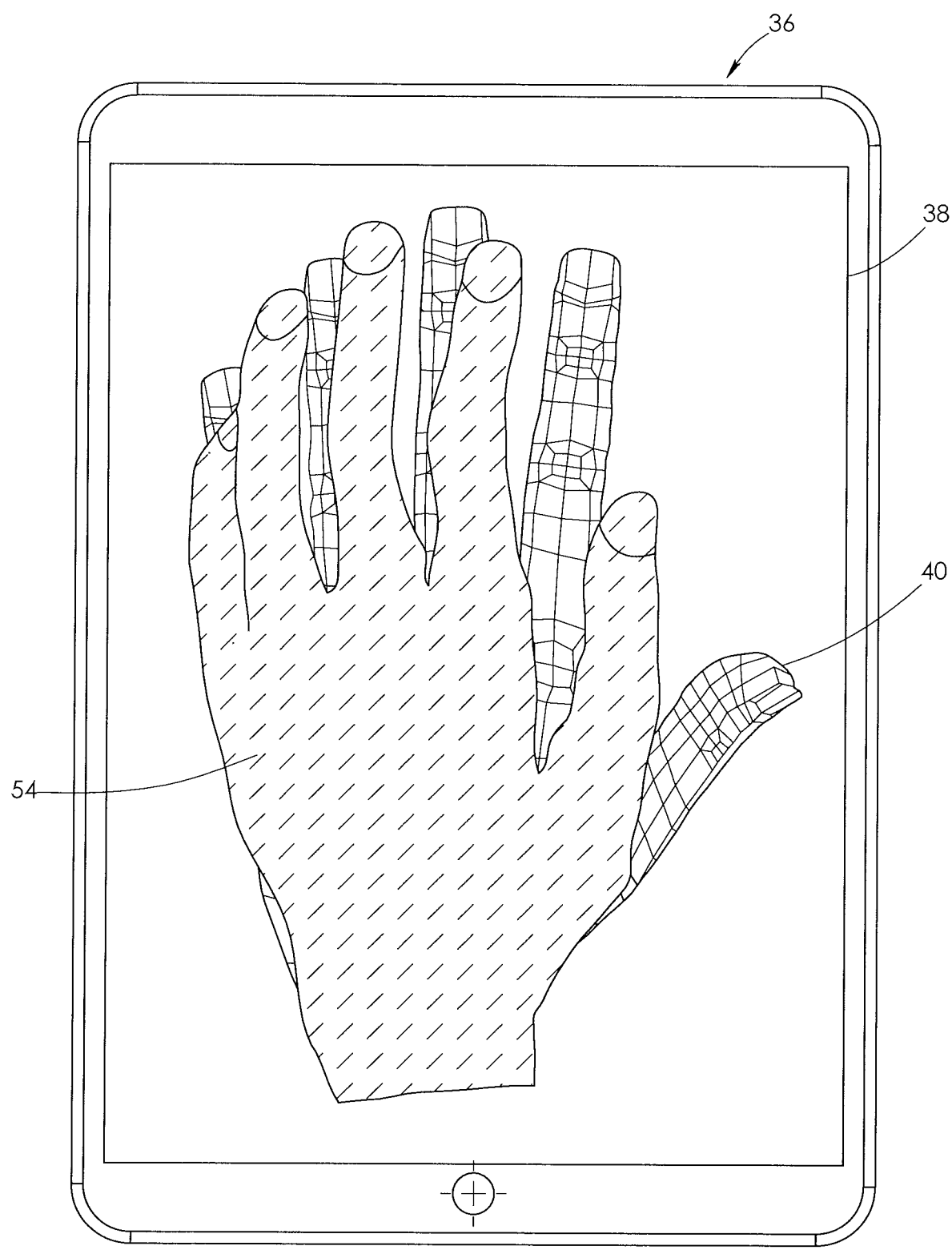
FIG. 6 is the computer shown in FIG. 4, with a virtual representation of a mapped envelope shown superimposed over the reference envelope. Portions of the mapped envelope are positioned outside of the boundaries of the reference envelope.
Figure 7:
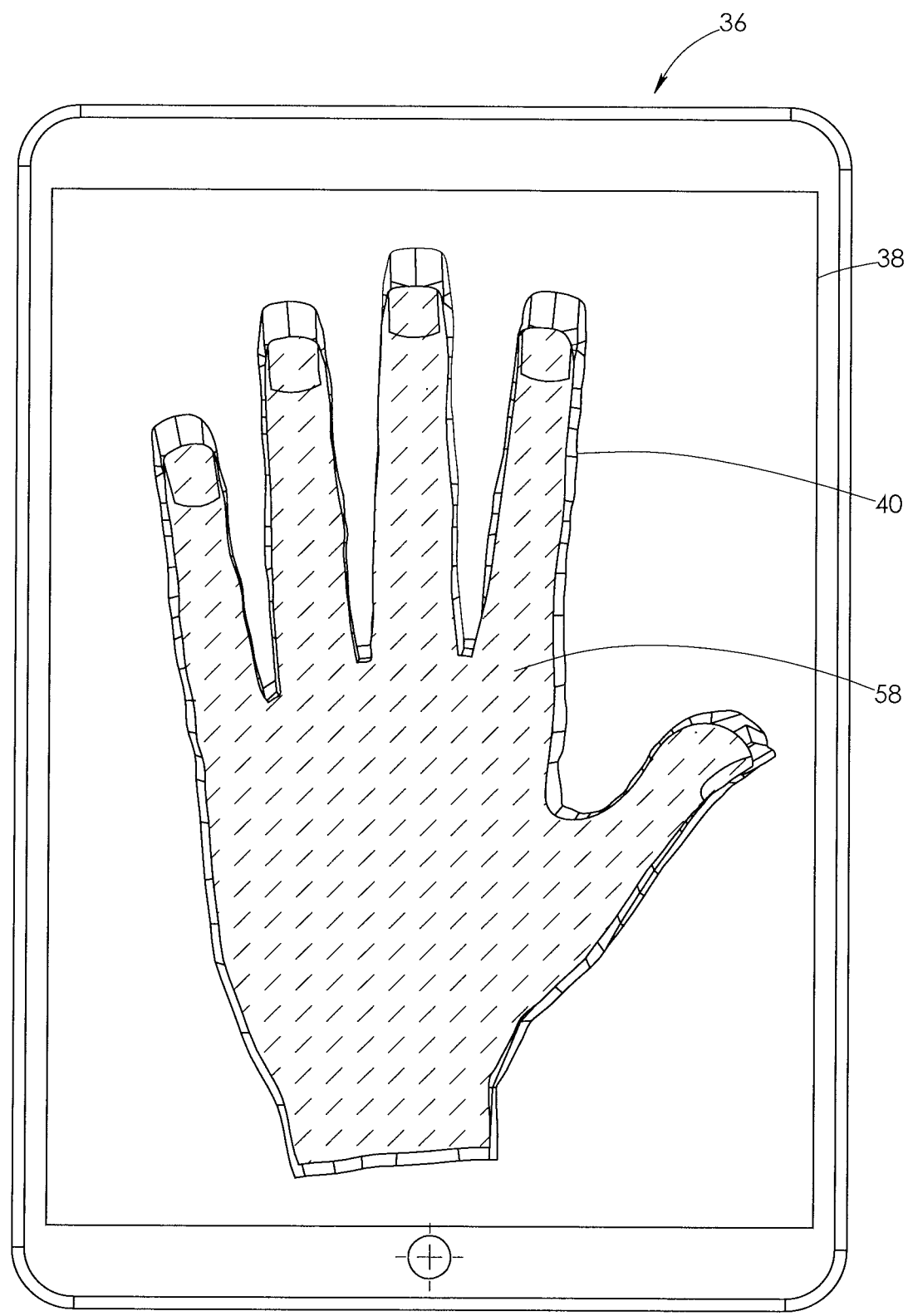
FIG. 7 is the same view as FIG. 6, but the mapped envelope is shown fully contained within the boundaries of the reference envelope.

Turning to FIGS. 5-7, in operation, the processor compares a selected reference envelope to a newly created mapped envelope of a patient's body part. In FIG. 5, for example, a patient 50 has his hand 52 placed below the x-ray emitter 12 and range sensor 28. The range sensor 28 will take measurements of everything within its field of view 30, including the hand 52, and send the collected data to the computer 36.

The computer's processor uses the collected data to generate a three-dimensional virtual map of the received data. The processor then generates an envelope that closely surrounds the body part depicted within the virtual map, creating a mapped envelope of the patient's body part. The mapped envelope of the patient's body part may exist only in coded form and not be visible to an x-ray operator 56. Alternatively, the mapped envelope may be configured so that a virtual image of the mapped envelope is displayed on the computer's monitor 38. For example, a virtual image of a mapped envelope 54 of the patient's hand 52 is shown superimposed over the reference envelope 40 in FIG. 6.

The processor compares the mapped envelope to the reference envelope and determines whether the mapped envelope is fully contained within the reference envelope. Such comparison may be displayed on the computer's monitor 38, as shown in FIGS. 6 and 7. Alternatively, the processor may make such comparison internally without visual representation.

The processor is configured to scale dimensions of the selected reference envelope to correspond with the size of the patient's body part as measured by the range sensor 28. For example, if the processor determines that the length of the patient's hand is longer than the reference envelope, the processor will appropriately extend the length the reference envelope. Likewise, the processor may enlarge or decrease the width and height of the reference envelope, as needed.

After any necessary scaling, the processor will determine if the mapped envelope is fully contained within the reference envelope and notify the x-ray operator 56 of its determination. If the processor determines that the mapped envelope is not fully contained within the reference envelope, the x-ray operator 56 will receive a negative notification. In contrast, if the processor determines that the mapped envelope is fully contained within the reference envelope, the x-ray operator 56 will receive a positive notification.

A negative notification indicates for the x-ray operator 56 that the patient's body part is not properly positioned and needs to be adjusted. In FIG. 6, for example, the fingers of the mapped envelope 54 are positioned outside of the boundaries of the reference envelope 40. If the x-ray image were captured with the patient's hand 52 in such position, a radiologist may have difficulty reading the image and properly diagnosing the patient.

Upon receiving a negative notification, the x-ray operator 56 will reposition the patient's body part. The range sensor 28 will again take measurements of the body part and transmit the collected data to the computer 36. The processor will create a new virtual map using the newly collected data, and subsequently create a new mapped envelope of the patient's body part. The new mapped envelope is then compared to the original reference envelope.

If the x-ray operator 56 receives another negative notification, the x-ray operator will again re-position the patient's body part and another new mapped envelope will be created. This process continues until the processor determines that the new mapped envelope is fully contained within the reference envelope and the x-ray operator receives a positive notification.

A positive notification indicates for the x-ray operator 56 that the patient's body part is properly positioned and ready to be x-rayed. In FIG. 7, for example, a new mapped envelope 58 is fully contained within boundaries of the reference envelope 40. An x-ray image of the patient's hand 52 in such position provides a Radiologist with better information for which to diagnose the patient 50.

During operation, the range sensor 28 will continually scan and measure objects within its field of view 30 and transmit the collected data to the computer 36, even if the processor already provided a positive notification. The computer 36 will continually generate new mapped envelopes of the body part upon receiving new data and continually compare such mapped envelopes to the selected reference envelope. Thus, if the patient 50, for example, moves his hand 52 immediately prior to the x-ray emitter 12 capturing an x-ray image, the x-ray operator 56 will receive a negative notification. Therefore, the system 10 may prevent the x-ray operator 56 from taking a wasted x-ray image and exposing the patient 50 to unnecessary radiation.

The processor may provide the x-ray operator 56 a positive or negative notification via an audible alarm and/or a notification displayed on the monitor 38. For example, the processor may cause the computer 36 to produce a "ding" noise for a positive notification and a buzzer noise for a negative notification. As another example, a green check mark for a positive notification or red "x" for a negative notification may be displayed on the monitor 38.

Figure 10:
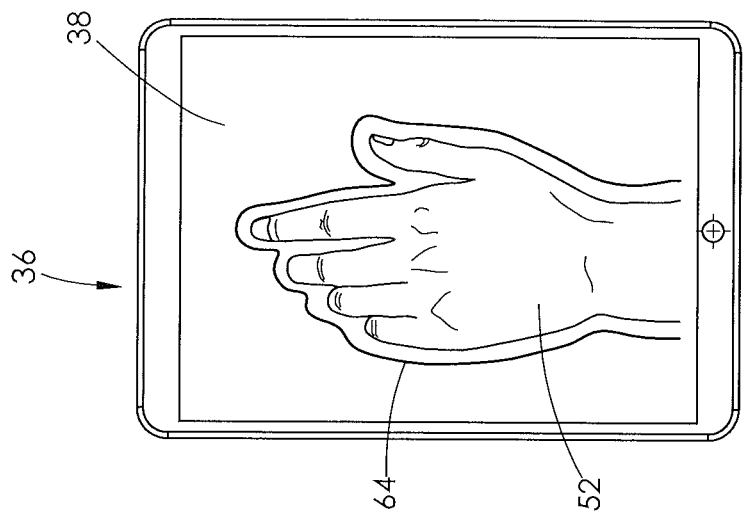
FIG. 10 is the same view as FIG. 9, but the hand has been slightly moved and is outlined by a solid line.
Figure 9:
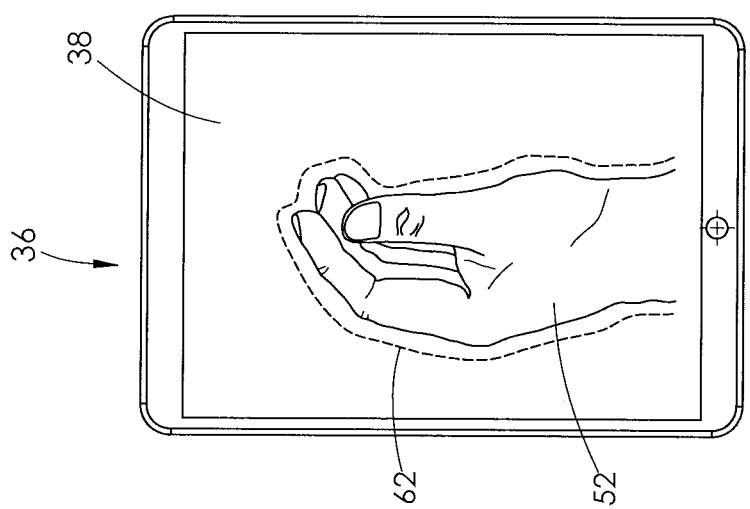
FIG. 9 is the same view shown in FIG. 8, but the hand has slightly moved and is still outlined in dashed lines.
Figure 8:
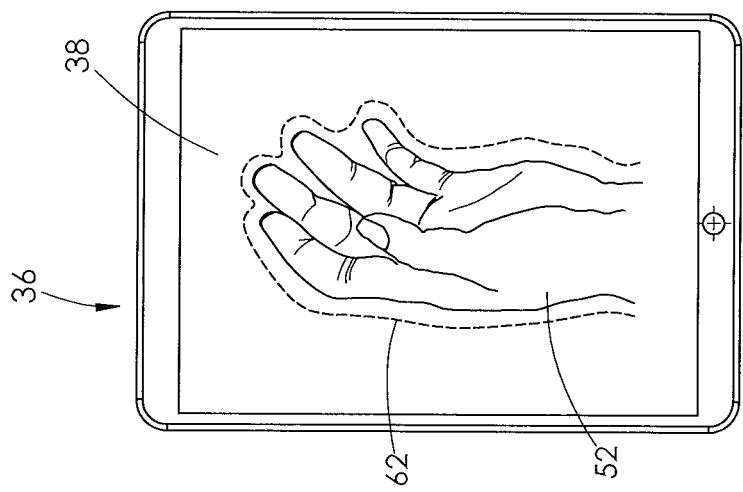
FIG. 8 is the computer shown in FIG. 2. A captured image of a patient's hand is displayed on the computer's monitor and is outlined in dashed lines.

With reference to FIGS. 8-10, if a camera 32 is used with the system 10, an image of the patient's body part within the camera's field of view 34 may be displayed on the monitor 38. For example, an image of the patient's hand 52 is shown in FIGS. 8-10. During operation, the processor may use any number of visual aids in conjunction with the displayed image to indicate a positive or negative notification. For example, the processor may outline the body part in dashed lines to indicate a negative notification and a solid line to indicate a positive notification. The hand 52 is outlined in dashed lines 62 in FIGS. 8 and 9, and a solid line 64 in FIG. 10. Different colors, shading, highlights, patterns, flashing lights or displayed words may also be used.

Figure 11:
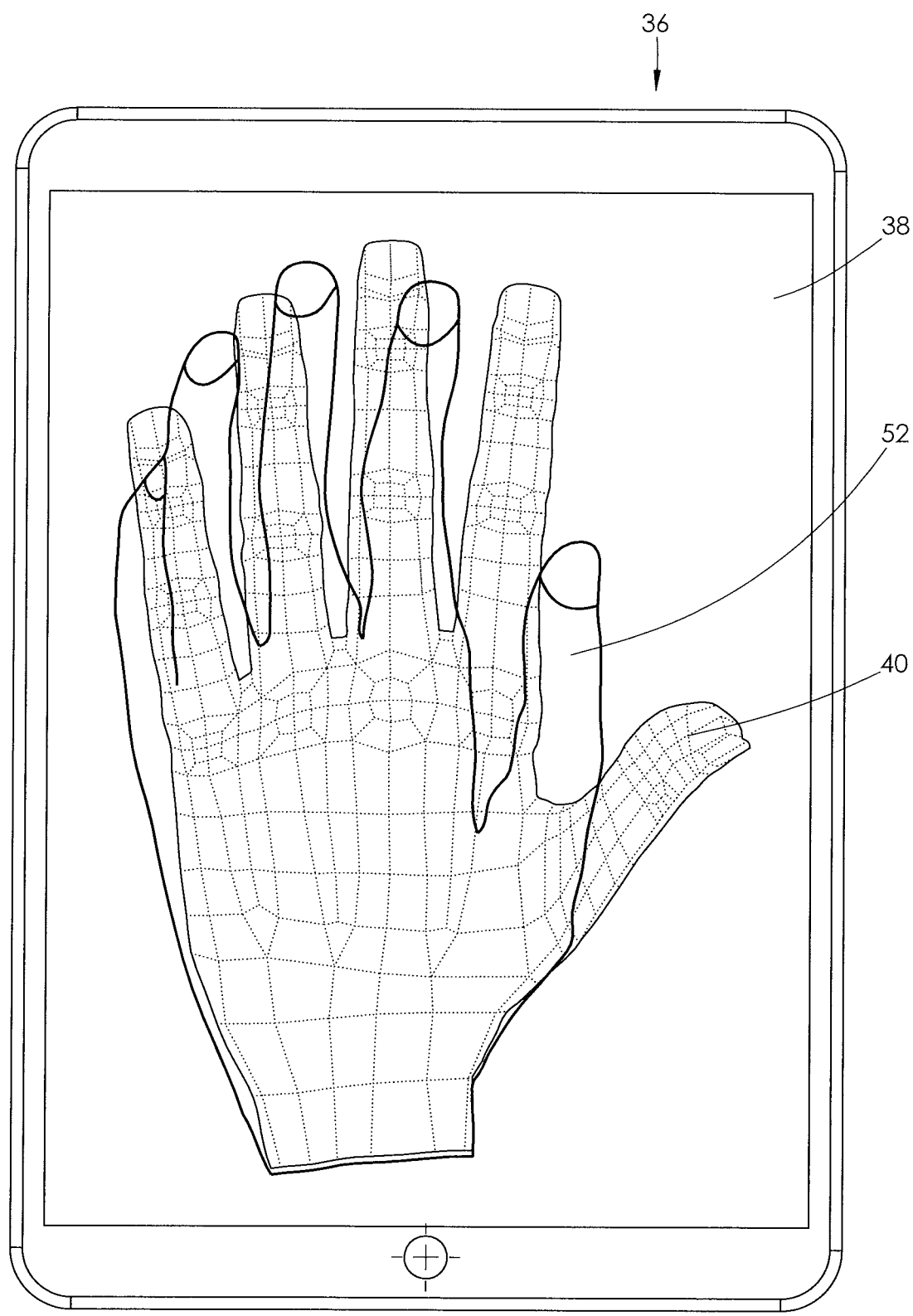
FIG. 11 is the computer shown in FIG. 2. The reference envelope of FIG. 4 is displayed superimposed over a captured image of a patient's hand on the computer's monitor.

In an alternative embodiment, a virtual image of the selected reference envelope may be superimposed over the image of the patient's body part displayed on the monitor. For example, the reference envelope 40 is shown superimposed over an image of the patient's hand 50 in FIG. 11. The processor may be configured to highlight the area of the body part that does not match the selected reference envelope. Showing the reference envelope in combination with an image of the patient's body part may help the x-ray operator properly position the patient.

In further alternative embodiments, a general outline of the selected reference envelope may be displayed on the computer's monitor to help the x-ray operator correctly position the body part. The outline may be superimposed over the image of the patient's body part displayed on the monitor.

Turning back to FIGS. 5-7, to use the system 10, an x-ray operator 56 will first position the patient's body part, such as the hand 52, for example, within the x-ray emitter's field of view 30. The operator 56 will subsequently select a reference envelope, like reference envelope 40, using the menu 42 displayed on the computer 36. Alternatively, the reference envelope may be selected prior to placing the patient's hand 52 below the x-ray emitter 12.

Once the desired reference envelope is selected and the patient's hand 52 is below the x-ray emitter 12, the system 10 will create a mapped envelope 54 of the hand 52. The processor compares the mapped envelope 54 of the hand 52 to the selected reference envelope 40. If the mapped envelope 54 is not fully contained within the reference envelope 40, as shown in FIG. 6, the processor will provide the x-ray operator 56 a negative notification. Once the processor determines that the hand 52 is properly positioned, as shown in FIG. 7, the processor will provide the x-ray operator 56 a positive notification, indicating that it is time to take an x-ray image. The x-ray operator 56 will subsequently signal the x-ray emitter 12 to capture an x-ray image.

If needed, the x-ray operator 56 will then move to a new view of the hand 52, such as a lateral view. The x-ray operator 56 will select a new reference envelope, corresponding to the desired view, and restart the process of positioning the patient's hand 52. This process will continue until the x-ray operator 56 captures all of the desired x-ray views of the patient's hand 52. Using the system 10, the x-ray operator 56 is able to capture a properly positioned, quality image of the patient's body part on the first attempt.

The captured x-ray images are subsequently sent to a radiologist for analysis and diagnosis. Alternatively, the captured x-ray images may be analyzed by an artificial intelligence (AI) system configured to diagnose the patient. The AI system may be built into the processor in order to provide a patient with an initial diagnosis immediately after having x-ray images taken.

Turning back to FIG. 1, the settings for the x-ray emitter 12 may be adjusted via a control panel 66 on a front end of the emitter 12 In an alternative embodiment of the system, the computer may be supported on the x-ray emitter and be in communication with the emitter's control panel. The x-ray operator may use the control panel to select a desired reference envelope. The comparison of a mapped envelope to a reference envelope may be performed internally by the computer's processor. Once the processor determines that the patient's body part is properly positioned, the computer's processor may cause lights to flash or an audible alarm to sound.

In further alternative embodiments, the reference envelope created by the processor may be only an outline of the exemplary body part, rather than a three-dimensional map. Likewise, the mapped envelope of the patient's body part created by the processor may also only be an outline of the patient's body part. In such embodiment, the processor compares the outline of the reference envelope to the outline of the mapped envelope to determine whether the mapped envelope is fully contained within the reference envelope.

The x-ray emitter 12 shown in FIG. 1 is just one type of x-ray machine that the different embodiments of the system described herein may be used with. In alternative embodiments, the system may be used with a chest x-ray machine/wall unit, portable x-ray machines or other type of x-ray machines known in the art. In further alternative embodiments, the system may be used with x-ray machines used in veterinary medicine. In such case, the reference envelopes would correspond to body parts of different animals, such as a dog or cat.

In further alternative embodiments, rather than adjust the position of the patient's body part until the mapped envelope is fully contained within the reference envelope, the position of the x-ray emitter may be adjusted. For example, if the patient's hand is positioned too far to the right, the x-ray emitter may be configured to automatically move to the right until the mapped envelope of the patient's hand is fully contained within the reference envelope. The x-ray emitter may be equipped with one or motors configured to move the x-ray emitter in a plurality of different directions and in precise increments. The motor may be in communication with the processor, which may direct movement of the motor based on the comparison of the mapped envelope to the reference envelope.

Changes may be made in the construction, operation and arrangement of the various parts, elements, steps and procedures described herein without departing from the spirit and scope of the invention as described in the following claims.

The invention claimed is:

1. A system, comprising:
   an x-ray emitter having a field of view;
   a three-dimensional range sensor having a field of view that at least partially overlaps the field of view of the x-ray emitter; and
   a processor having a memory within which a plurality of reference envelopes are stored, the processor is in communication with the range sensor and is configured to use data from the range sensor to generate a virtual map that includes a body part within the field of view of the range sensor, to generate within the virtual map an envelope that closely surrounds the body part, and to compare the mapped envelope to a selected reference envelope.

2. The system of claim 1 in which the reference envelope is selected in response to input from a human user of the system.

3. The system of claim 1 in which the comparison performed by the processor determines whether the mapped envelope is fully contained within the selected reference envelope.

4. The system of claim 1, further comprising:
a monitor in communication with the processor, the monitor configured to display, in real time and in superposition, representations of the body part within the field of view of the sensor and the selected reference envelope.

5. The system of claim 1, further comprising:
an optical camera having a field of view that at least partially overlaps the field of view of the x-ray emitter.

6. The system of claim 5, further comprising:
a monitor in communication with the processor, the monitor configured to display, in real time and in superposition, representations of the body part within the field of view of the optical camera and the selected reference envelope.

7. The system of claim 3, further comprising:
a notification system controlled by the processor that sends a signal to a human user of the system if the mapped envelope is fully contained within the selected reference envelope.

8. The system of claim 7 in which the signal sent by the notification system is an audible signal.

9. The system of claim 7 in which the signal sent by the notification system is a visual signal.

10. The system of claim 9 in which the visual signal comprises a flashing light.

11. The system of claim 3, further comprising:
a notification system controlled by the processor that sends a signal to a human user of the system if the mapped envelope is not fully contained within the selected reference envelope.

12. The system of claim 11 further comprising:
a monitor in communication with the processor, the monitor configured to display, in real time and in superposition, representations of the body part within the field of view of the sensor and the selected reference envelope; and
in which the signal sent by the notification system is displayed on the monitor.

13. The system of claim 1 further comprising:
an interface in communication with the processor and comprising a menu listing a plurality of different body parts and a plurality of different x-ray views.

14. The system of claim 13 in which the reference envelope is selected in response to input from a human user of the system, in which the input selects one of the plurality of different body parts and one of the plurality of different x-ray views on the menu.

15. The system of claim 1 in which the plurality of reference envelopes include reference envelopes for a plurality of different body parts.

16. The system of claim 1 in which the range sensor is a time-of-flight sensor.

17. The system of claim 1 in which the processor is configured to scale dimensions of the selected reference envelope based on the dimension of the mapped envelope.

18. A method of using the system of claim 1, comprising:
positioning the body part within the field of view of the x-ray emitter and the range sensor;
selecting one of the plurality of reference envelopes;
signaling a human user of the system if the mapped envelope is fully contained within the selected reference envelope; and
capturing one or more x-ray images of the body part.

19. The method of claim 18, further comprising:
after the selecting step, adjusting the body part until the mapped envelope is fully contained within the selected reference envelope.

20. The method of claim 18 in which each of the plurality of reference envelopes are created by the steps of:
generating a virtual map of an exemplary body part; and
generating an envelope within the virtual map that closely surrounds the exemplary body part.

* * * * *